United States Patent [19]

De Luca

[11] 4,370,165

[45] Jan. 25, 1983

[54] LOW SILVER DENTAL AMALGAM ALLOY COMPOSITION

[75] Inventor: Robert De Luca, Pennington, N.J.

[73] Assignee: Johnson & Johnson Dental Products Company, East Windsor, N.J.

[21] Appl. No.: 265,883

[22] Filed: May 21, 1981

[51] Int. Cl.³ .............................................. C09K 3/00
[52] U.S. Cl. ...................................... 106/35; 420/502
[58] Field of Search ......................... 106/35; 75/173 C

[56] References Cited

U.S. PATENT DOCUMENTS

| | | | |
|---|---|---|---|
| 3,963,484 | 6/1976 | Sarkar | 75/173 C |
| 3,980,472 | 9/1976 | Asgar et al. | 75/173 C |
| 3,997,328 | 12/1976 | Greener | 75/173 C |
| 3,997,329 | 12/1976 | Aliotta et al. | 75/173 C |
| 3,997,330 | 12/1976 | Aliotta et al. | 75/173 C |

OTHER PUBLICATIONS

Peyton, A. F.; *Restorative Dental Materials*, 1968, 3rd Edition, p. 375.

*Primary Examiner*—Theodore Morris
*Attorney, Agent, or Firm*—Charles J. Metz

[57] ABSTRACT

A composition adapted for amalgamation with mercury to form a dental amalgam, which consists essentially of a uniform mixture of:
(a) A first alloy composed of at least 65 weight percent silver, up to 29 weight percent tin, up to 6 weight percent copper, and up to 2 weight percent zinc; and
(b) A second alloy composed of from 46 to 51 weight percent silver, from 4 to 6 weight percent tin, and from 45 to 48 weight percent copper.

3 Claims, No Drawings

LOW SILVER DENTAL AMALGAM ALLOY COMPOSITION

The invention relates to a new dental amalgam alloy composition having an excellent balance of properties and a relatively low silver content.

BACKGROUND OF THE INVENTION

Most Class II dental restorations, i.e., those on the grinding surface of molars, employ amalgams which typically contain approximately equal proportions, by weight, of mercury and a high silver amalgam alloy. Conventional amalgam alloys are usually based upon on alloy having the following composition, by weight:
   Silver, at least 65 percent
   Tin, up to 29 percent
   Copper, up to 6 percent
   Zinc, up to 2 percent However, this standard alloy is now rarely, if ever, used by itself as a dental amalgam alloy because significant amounts of the readily corrodible tin-mercury gamma-2 phase forms when it is amalgamated. For this reason, a considerable amount of research has been done to find alloys that can be blended with the standard alloy and still maintain adequate working time and acceptable physical properties.

The present invention provides an amalgam alloy blend wherein the said standard alloy is mixed with a second alloy to produce an amalgam alloy having adequate working time, acceptable physical properties, and as an added bonus, a slight but significant reduction in the proportion of the increasingly expensive silver in the alloy.

SUMMARY OF THE INVENTION

The invention provides a composition adapted for amalgamation with mercury to form a dental amalgam, which consists essentially of a uniform mixture of:

(a) A first alloy composed of at least 65 weight percent silver, up to 29 weight percent tin, up to 6 weight percent copper, and up to 2 weight percent zinc; and (b) A second alloy composed of from 46 to 51 weight percent silver, from 4 to 6 weight percent tin, and from 45 to 48 weight percent copper, Wherein, when said composition is mixed with mercury, the resulting dental amalgam has the following properties:

1-hour compressive strength, at least 16,000 psi; 24 hour compressive strength, at least 50,000 psi; percent flow, less than 1; dimensional change, less than ±15 microns/centimeter; creep, less than 0.5 percent; and working time, 2 to 6 minutes, The said components (a) and (b) being present in proportions of from 33 to 67 weight percent (a) and from 67 to 33 weight percent (b), the percentage being based on weight of (a) plus (b).

PRIOR ART

Sarkar, in U.S. Pat. No. 3,963,484, discloses an amalgam alloy blend consisting of 70 to 90 weight percent of the standard silver/tin/copper/zinc alloy described above, and from 10 to 30 weight percent of a high copper alloy, including one of the following composition:
   Silver, up to 49 percent;
   Tin, up to 10 percent;
   Copper, balance.

Other U.S. Patents which describe various dental amalgam alloys include Weikel, U.S. Pat. No. 3,954,457, Asgar et al, U.S. Pat. No. 3,980,472, Greener, U.S. Pat. No. 3,997,328 and Aliotta et al, U.S. Pat. Nos. 3,997,329 and 3,997,330.

DETAILED DESCRIPTION OF THE INVENTION

The first of the two alloys used in this invention has the following composition by weight:
   Silver, at least 65 percent;
   Tin, up to 29 percent;
   Copper, up to 6 percent;
   Zinc, up to 2 percent.

This alloy is used in the blend in proportions of about 33 to 67 weight percent.

The second alloy is a silver/copper/tin alloy of the following composition, by weight:
   Silver: 46-51 percent;
   Copper: 45-48 percent;
   Tin: 4-6 percent.

This alloy is used in the blend in proportions of from 67 to 33 weight percent.

Both of the alloys may be employed in the usual form of atomized powders, lathe-cut particles, filings, or pressed tablets made therefrom.

The two powders are intimately and uniformly blended prior to mixing with mercury. The alloy blend is used with mercury in the customary proportions, i.e., from about 40 to 60 weight percent of the blend, and from about 60 to 40 weight percent mercury.

The following examples illustrate the invention:

EXAMPLES 1-3 AND CONTROL EXAMPLES 1-2

Two alloy powders were produced by atomization of molten alloy. The powders passed through 200 mesh, and therefore had particle sizes of less than 75 microns. Their compositions were the following.

| Alloy A | Weight % |
| --- | --- |
| Silver | 65.66 |
| Tin | 27.65 |
| Copper | 3.95 |
| Zinc | 1.80 |

| Alloy B | Weight % |
| --- | --- |
| Silver | 48.40 |
| Copper | 46.39 |
| Tin | 5.17 |

The two alloys were blended in various proportions and each blend was triturated for 10 seconds with mercury in proportions of 50 weight percent blend and 50 weight percent mercury. Physical properties of the resulting amalgam were the following:

TABLE I

| PROPERTY | CONTROL 1 | EX. 1 | EX. 2 | EX. 3 | CONTROL[(1)] 2 |
| --- | --- | --- | --- | --- | --- |
| % A/B | 100A | 33A / 67B | 50A / 50B | 67A / 33B | — |
| 1 hr. comp. strength (psi) | 23,200 | 25,300 | 27,600 | 19,900 | 22,000 |
| 24 hr. comp. strength (psi) | 63,500 | 49,400 | 62,800 | 62,300 | 60,000 |
| % Flow | 0.79 | 0.19 | 0.28 | 0.53 | 0.6 |
| Dimensional Change (um/cm) | −16.0 | +1.5 | +0.3 | −5.2 | −6.0 |
| Creep (%) | 0.12 | 0.14 | 0.20 | 0.25 | 0.25 |

TABLE I-continued

| PROPERTY | CONTROL 1 | EX. 1 | EX. 2 | EX. 3 | CONTROL[1] 2 |
|---|---|---|---|---|---|
| Working Time, Minutes | 7.0 | 6 | 3.5 | 3.5 | 2 to 4 |

[1] A commercial dental amalgam alloy described by Youdelis in U.S. Pat. No. 3,305,356.

The test procedures employed to evaluate physical properties were known procedures. Brief outlines of the principles of each procedure are the following:

Compression Strength

A freshly prepared right cylinder, 4 mm. in diameter by 8 mm., of the amalgam, after conditioning at 37° C. for 1 hour or 24 hours, is stressed in the compression mode parallel to the long axis until failure occurs, and the force necessary to establish this fracture point is determined.

Percent Flow

A right cylinder, 4 mm. diameter by 8 mm. of dental amalgam, after conditioning at 37° C.±1.0° C. for three hours, is subjected to a constant axial compression load of 10.0 meganewtons per square meter for 21 hours. The shortening obtained by subtracting the measured length after loading from the measured length before loading is calculated as percent flow.

Dimensional Change

A freshly prepared right cylinder, 4 mm. diameter by 8 mm., of amalgam is measured five minutes after trituration. The sample is then conditioned for 24 hours at 37° C. and measured again. The setting contraction or expansion in the length dimension is then reported as microns per centimeter.

Creep

A right cylinder, 4 mm. diameter by 8 mm., of amalgam is conditioned for 7 days at 37° C. It is then subjected to a constant axial compression load of 36.0 meganewtons per square meter for 4 hours. The specimen is removed from the load and measured. The change in the axial dimension is reported as percent creep.

Working Time

This test is based upon the principle that when the amalgam can no longer be formed into a cohesive plastic mass, the set or working time has been reached. After triturating for 10 seconds, any pestle is removed from the capsule containing the amalgam. The triturator is then turned on again for 1 second, which will form the amalgam into a ball. This is repeated after 1½ minutes, and then every 30 seconds, until the 1 second trituration causes the ball to crumble.

Control Examples 3–5

Two parts, by weight, of a powder of the following alloy:

| Silver | 68 weight percent |
|---|---|
| Tin | 27 weight percent |
| Copper | 3.5 weight percent |
| Zinc | 1.5 weight percent | were blended with 1 part of each of the alloys displayed on Table II, to form blends that were mixed with equal weights of mercury. The resulting amalgams were triturated for 10 seconds, and were evaluated for physical properties, as shown in Table II:

TABLE II

| Alloy Composition, | Control Example No. | | |
|---|---|---|---|
| | 3 | 4 | 5 |
| Silver | 50.75 | 50.7 | 71.61 |
| Tin | — | 0.085 | 0.15 |
| Copper | 48.99 | 49.18 | 28.13 |
| 1 hr. comp. strength, psi | 4,300 | 6,300 | 10,600 |
| 24 hr. comp. strength, psi | 59,300 | 69,100 | 60,300 |
| % Flow | 1.53 | 3.12 | 1.49 |
| Dimensional Change, um/cm | — | −16 | −3.5 |
| Creep, % | 0.27 | 0.68 | 0.29 |
| Working Time, minutes | over 10 | over 10 | 6 |

What is claimed is:

1. A composition adapted for amalgamation with mercury to form a dental amalgam, which consists essentially of a uniform mixture of:
   (a) A first alloy composed of at least 65 weight percent silver, up to 29 weight percent tin, up to 6 weight percent copper, and up to 2 weight percent zinc; and
   (b) A second alloy composed of from 46 to 51 weight percent silver, from 4 to 6 weight percent tin, and from 45 to 48 weight percent copper,
   wherein, when said composition is mixed with from 40 to 60 weight percent memory, based on weight of said composition plus mercury, the resulting dental amalgam has the following properties:
   1-hour compressive strength, at least 16,000 psi; 24 hour compressive strength, at least 50,000 psi; percent flow, less than 1; dimensional change, less than ±15 microns/centimeter; creep, less than 0.5 percent; and working time, from 2 to 6 minutes,
   the said components (a) and (b) being present in proportions of from 33 to 67 weight percent (a) and from 67 to 33 weight percent (b), the percentage being based on weight of (a) plus (b).
2. The composition of claim 1 wherein the components (a) and (b) are employed in approximately equal proportions, by weight.
3. A dental amalgam produced by mixing the composition of claim 1 with mercury.

* * * * *